(12) United States Patent
Peiffer et al.

(10) Patent No.: US 6,194,622 B1
(45) Date of Patent: Feb. 27, 2001

(54) METHOD FOR INHIBITING HYDRATE FORMATION

(75) Inventors: Dennis G. Peiffer, Annandale, NJ (US); Christine A. Costello, Easton, PA (US); Lawrence D. Talley, Friendswood, TX (US); Pamela J. Wright, Easton, PA (US)

(73) Assignee: ExxonMobil Upstream Research Company, Houston, TX (US)

( * ) Notice: Subject to any disclaimer, the term of this patent is extended or adjusted under 35 U.S.C. 154(b) by 0 days.

(21) Appl. No.: 09/266,387

(22) Filed: Mar. 11, 1999

Related U.S. Application Data

(60) Provisional application No. 60/088,709, filed on Jun. 10, 1998.

(51) Int. Cl.$^7$ .................................. C07C 7/20; F17D 1/05
(52) U.S. Cl. .................................. 585/15; 585/950; 95/153
(58) Field of Search .................. 585/15, 905; 95/153

(56) References Cited

U.S. PATENT DOCUMENTS

| | | | |
|---|---|---|---|
| H1749 | 9/1998 | Colle et al. | 585/15 |
| 4,132,535 | 1/1979 | Rivers, Jr. et al. | 55/23 |
| 4,856,593 | 8/1989 | Matthews et al. | 106/310 |
| 4,915,176 | 4/1990 | Sugier et al. | 166/371 |
| 4,973,775 | 11/1990 | Sugier et al. | 585/15 |
| 5,036,136 | 7/1991 | Peiffer | 524/812 |
| 5,244,878 | 9/1993 | Sugier et al. | 507/90 |
| 5,276,248 * | 1/1994 | Engelhardt et al. | 585/899 |
| 5,331,105 | 7/1994 | Duncum et al. | 585/800 |
| 5,420,370 | 5/1995 | Sloan, Jr. | 585/15 |
| 5,426,258 | 6/1995 | Thomas et al. | 585/15 |
| 5,432,292 | 7/1995 | Sloan, Jr. | 585/15 |
| 5,434,323 | 7/1995 | Durand et al. | 585/15 |
| 5,491,269 | 2/1996 | Colle et al. | 585/15 |
| 5,583,273 | 12/1996 | Colle et al. | 585/15 |
| 5,600,044 | 2/1997 | Colle et al. | 585/15 |
| 5,639,925 | 6/1997 | Sloan, Jr. et al. | 585/15 |
| 5,744,665 | 4/1998 | Costello et al. | 585/15 |
| 5,789,635 | 8/1998 | Durand et al. | 585/15 |
| 5,817,898 | 10/1998 | Delion et al. | 585/15 |
| 5,841,010 | 11/1998 | Rabeony et al. | 585/3 |
| 5,874,660 | 2/1999 | Colle et al. | 585/15 |
| 5,880,319 * | 3/1999 | Sloan, Jr. | 585/15 |
| 5,900,516 | 5/1999 | Talley et al. | 585/15 |
| 5,981,816 * | 11/1999 | Sinquin et al. | 585/15 |
| 6,015,929 | 1/2000 | Rabeony et al. | 585/15 |
| 6,028,233 * | 2/2000 | Colle et al. | 585/15 |

FOREIGN PATENT DOCUMENTS

| | | |
|---|---|---|
| 2178366 | 12/1996 | (CA) . |
| 0 457 375 A1 | 11/1991 | (EP) . |
| 0 812307 B1 | 12/1998 | (EP) . |
| WO 93/25798 | 12/1993 | (WO) . |
| 96/41786 | 12/1996 | (WO) . |

OTHER PUBLICATIONS

SU 1391–692A (Abstract) Nov. 26, 1986.
A. M. Kuliev et al,; 1972; Studies of surfactants as anti–hydrate inhibitors.
Kalogerakis, N.; Effect of Surfactants on Hydrate Formation Kinetics; SPE 25188; Mar. 1993.

* cited by examiner

Primary Examiner—Walter D. Griffin
(74) Attorney, Agent, or Firm—Denise Y. Wolfs

(57) ABSTRACT

A method for inhibiting the formation of gas hydrates in a petroleum fluid having hydrate-forming constituents is claimed. More specifically, the method can be used to treat a petroleum fluid, such as natural gas conveyed in a pipe, to inhibit the formation of a hydrate flow restriction in the pipe. The hydrate inhibitors used for practicing the method comprise substantially water soluble homopolymers and copolymers of surfactant monomers, wherein the surfactant monomer unit may be represented by the formula:

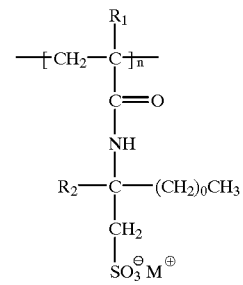

where $R_1$ and $R_2$ independently are hydrogen or a methyl group, M is a metal cation, n is a number sufficient to produce a number average molecular weight between 1000 and 6,000,000, and o is a number from 1 to 5.

20 Claims, No Drawings

METHOD FOR INHIBITING HYDRATE FORMATION

This application claims the benefit of U.S. Provisional Application Ser. No. 60/088,709, filed on Jun. 10, 1998.

FIELD OF THE INVENTION

The present invention relates to a method for inhibiting the formation of clathrate hydrates in a fluid. More specifically, the invention relates to a method for inhibiting the formation of gas hydrates in a pipe used to convey oil or gas.

BACKGROUND OF THE INVENTION

Petroleum fluids typically contain carbon dioxide and hydrogen sulfide, as well as various hydrocarbons, such as methane, ethane, propane, normal butane and isobutane. Water, present as a vapor and/or as a liquid phase, is also typically found mixed in varying amounts with such hydrocarbons. Under conditions of elevated pressure and reduced temperature, clathrate hydrates can form when such petroleum fluids contain water. Clathrate hydrates are water crystals which form a cage-like structure around "guest" molecules such as hydrate-forming hydrocarbons or other gases. Some hydrate-forming hydrocarbons include, but are not limited to, methane, ethane, propane, isobutane, butane, neopentane, ethylene, propylene, isobutylene, cyclopropane, cyclobutane, cyclopentane, cyclohexane, and benzene. Other gases which may form hydrates include, but are not limited to, oxygen, nitrogen, hydrogen sulfide, carbon dioxide, sulfur dioxide, and chlorine.

Gas hydrate crystals or gas hydrates are a class of clathrate hydrates of particular interest to the petroleum industry because of the pipeline blockages that they can produce during the production and/or transport of natural gas and other petroleum fluids. For example, at a pressure of about 1000 kPa (145 psi), ethane can form gas hydrates at temperatures below 4° C. (39° F.), and at a pressure of 3000 kPa (435 psi), ethane can form gas hydrates at temperatures below 14° C. (57° F.). Such temperatures and pressures are not uncommon for many operating environments where natural gas and other petroleum fluids are produced and transported.

As gas hydrates agglomerate, they can produce hydrate blockages in the pipe or conduit used to produce and/or transport natural gas or other petroleum fluids. The formation of such hydrate blockages can lead to a shutdown in production and thus substantial financial losses. Furthermore, restarting a shutdown facility, particularly an offshore production or transport facility, can be difficult because significant amounts of time, energy, and materials, as well as various engineering adjustments, are often required to safely remove the hydrate blockage.

A variety of measures have been used by the oil and gas industry to prevent the formation of hydrate blockages in oil or gas streams. Such measures include maintaining the temperature and/or pressure outside hydrate formation conditions and introducing an antifreeze such as methanol, ethanol, propanol, or ethylene glycol. From an engineering standpoint, maintaining temperature and/or pressure outside hydrate formation conditions often requires design and equipment modifications, such as insulated or jacketed piping. Such modifications are costly to implement and maintain. The amount of antifreeze required to prevent hydrate blockages is typically between 10% to 30% by weight of the water present in the oil or gas stream. Consequently, several thousand gallons per day of such antifreeze can be required. Such quantities present handling, storage, recovery, and potential toxicity issues. Moreover, these solvents are difficult to completely recover from the production or transportation stream.

Consequently, there is a need for a gas hydrate inhibitor that can be conveniently mixed at low concentrations in the produced or transported petroleum fluids. Such an inhibitor should reduce the rate of nucleation, growth, and/or agglomeration of gas hydrate crystals in a petroleum fluid stream and thereby inhibit the formation of a hydrate blockage in the pipe conveying the petroleum fluid stream. As discussed more fully below, the inhibitors of this invention can effectively treat a petroleum fluid having a water phase, or a petroleum fluid containing water vapor that may condense to form a water phase, depending upon the operating environment.

The use of polymeric inhibitors has been proposed, however, these materials have a tendency to precipitate out of solution at higher temperatures. This is an undesirable characteristic, since the inhibitor must stay in solution under a wide range of temperatures to be most effective. The surfactant monomers described herein yield homopolymers and copolymers with good inhibition properties as well as better solubility at higher temperatures.

SUMMARY OF THE INVENTION

According to the invention, there is provided a method for inhibiting the formation of clathrate hydrates in a fluid having hydrate-forming constituents. One embodiment of the method comprises contacting the fluid with an inhibitor comprising a polymer or copolymer which has been made from surfactant monomer(s). In an alternative embodiment, the fluid is treated with a copolymer of the surfactant monomer copolymerized with a comonomer that is known, when polymerized with itself, to exhibit hydrate inhibition.

The polymers and copolymers of the invention can be classified as "polysurfactants" and are characterized by the general formula:

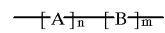

where the sum of n and m is an average number sufficient to produce a number average molecular weight between about 1,000 to about 6,000,000, and A is the following surfactant "mer-unit":

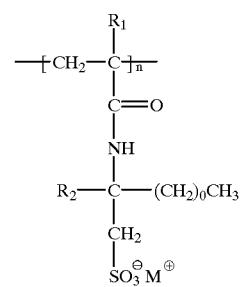

where both $R_1$ and $R_2$ are independently hydrogen or a methyl group, and o is a number from 1 to 5. Preferably, o is a number from 1 to 3, and more preferably, o is a number from 1 to 2.

The term "mer-unit" is used to describe both the monomers that are reacted to form polymers, and the polymer units that result from the conversion of one type of polymer units into another type of polymer units, by some reaction or conversion which occurs subsequent to the polymerization reaction.

M is a metal cation selected from the group consisting of metals of Group IA of the Periodic Table, preferably sodium and potassium, and an ammonium cation. Sodium is most preferred. The corresponding anionic group is a sulfonate group, as shown above, but alternatively may be a sulfinate, sulfate, phosphonate, phosphinate, phosphate, or carboxylate group. Sulfonate and carboxylate groups are preferred, and sulfonate groups are most preferred. The two ionic groups are preferably associated as salts.

B may be a surfactant mer-unit that is the same as, or a variant of, A. Alternatively, B is a monomer or mer-unit that is known, when polymerized with itself, to exhibit hydrate inhibition. For example, B may be an N-vinyl amide, an N-allyl amide, an acrylamide or methacrylamide, an N-vinyl lactam, a maleimide, or a vinyl oxazoline (a ring-closed cyclic imino ether).

The A and B mer-unit proportions, or mole ratio of m to n, can vary. The mole ratio m:n may vary from about 5:95 to about 95:5, or from about 25:75 to about 75:25, or from about 45:55 to about 55:45. Ratios which provide the most effective inhibitors for a given system are preferred.

The polymers and copolymers consistent with the description above form a class of materials designated "polysurfactants." By polysurfactants, we mean that there are pendant groups on the polymer backbone that resemble surfactant-like materials, i.e., there is a hydrophilic portion and a hydrophobic portion. The polysurfactants of the invention fall within the generic class of amphoteric polymers, those which contain hydrophilic and hydrophobic groups on the same mer-unit. An example is shown below for the case of the $C_6$ polysurfactant:

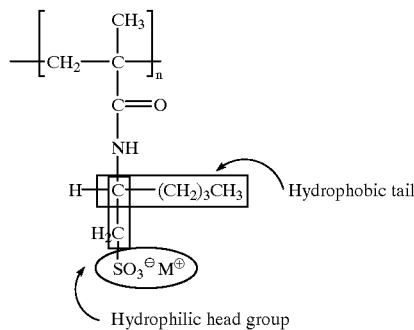

The designation of "$C_6$ polysurfactant" is based upon the number of carbon atoms below the nitrogen atom in the pendant group in the formula above, which results from the α-olefin used to produce the surfactant mer-unit. To obtain an effective hydrate inhibitor, it is important to properly balance the hydrophobic and hydrophilic nature of the mer-unit, such that the resulting polysurfactant is substantially water soluble.

DETAILED DESCRIPTION OF THE INVENTION

Inventive Method

The inventive method of the invention inhibits the formation of clathrate hydrates in a fluid having hydrate-forming constituents. Formation of clathrate hydrates means the nucleation, growth, and/or agglomeration of clathrate hydrates. Such clathrate hydrates may be formed in a fluid whether it is flowing or substantially stationary, but are most problematic in flowing fluids conveyed in a pipe. For example, flow restrictions arising from partial or complete blockages in a fluid can arise as clathrate hydrates adhere to and accumulate along the inside wall of the pipe used to convey the fluid. In addition, the invention can be used for inhibiting formation of clathrate hydrates in substantially stationary fluids.

In one embodiment of the invention, a concentrated solution or mixture of one or more of the inhibitors of the invention is introduced into a petroleum fluid. The term petroleum fluid includes fluids that are gases and/or liquids when under standard conditions, such as natural gas, crude oil, and various petroleum product streams. As the inhibitor solution of the invention is substantially dispersed in the fluid, it reduces the rate that clathrate hydrates are formed, and thereby reduces the tendency for a flow restriction to occur.

In a preferred embodiment, the solid inhibitor is first dissolved into an appropriate carrier solvent or liquid to make a concentrated solution or mixture. Alternatively, the inhibitor may be provided in a solution where it is left as dissolved in its polymerization reaction solvent. The solvent will preferably dissolve the inhibitor and, for convenience, such liquids are referred to hereafter as solvents, whether they produce an inhibitor solution, emulsion, or other type of mixture. The carrier solvent's principal purpose is to act as a carrier for the inhibitor and to facilitate the inhibitor's dispersion into the petroleum fluid. Any solvent suitable for delivering the inhibitor to the petroleum fluid may be used. Such carrier solvents include, but are not limited to, water, brine, sea water, produced water, methanol, ethanol, propanol, isopropanol, glycol, or mixtures of such solvents. Other solvents familiar to those skilled in the art may also be used. Aqueous solvents (water, brine, sea water, produced water) are preferred.

It should be understood that the use of a carrier solvent is not required to practice the invention, but it is a convenient method of introducing and dispersing the inhibitor into the fluid. In many applications, the use of a carrier solvent will facilitate treatment of the fluid stream. As noted above, water is frequently present along with hydrocarbons and other gases present in petroleum fluids. The presence of an aqueous phase in a petroleum fluid is not essential, but if present, will facilitate the dispersion of the inhibitor within the petroleum fluid. The presence of a significant aqueous phase in the petroleum fluid may reduce or eliminate the amount of carrier solvent required for dispersion of the inhibitor.

Any convenient concentration of inhibitor in the carrier solvent can be used, so long as it results in the desired final concentration in the aqueous phase of the petroleum fluid. Higher concentrations are preferred, since they result in a reduced volume of concentrated solution to handle and introduce into the petroleum fluid. The actual concentration used in a specific application will vary depending upon the selection of carrier solvent, the chemical composition and molecular weight of the inhibitor, the system temperature, the inhibitor's solubility in the carrier solvent at application conditions, and the presence of an aqueous phase in the petroleum fluid. If there is no aqueous phase present in the petroleum fluid, a dilute solution may be preferred.

The inhibitor mixture is introduced into the petroleum fluid using mechanical equipment, such as a chemical injection pump or other device which will be apparent to those skilled in the art. However, such equipment is not essential to practicing the invention. To ensure an efficient and effective treatment of the petroleum fluid with the inhibitor mixture, two factors should be considered.

First, an aqueous phase is preferably present at the location the inhibitor solution is introduced into the fluid. In some petroleum fluid systems (particularly natural gas systems), an aqueous phase does not appear until the gas has cooled sufficiently for water to condense. If this is the case, the inhibitor solution is preferably introduced after the water has condensed. Alternatively, in the event that an aqueous phase is not available at the point the inhibitor solution is introduced, the inhibitor solution concentration should be selected to ensure that the inhibitor solution's viscosity is sufficiently low to facilitate its dispersion throughout the petroleum fluid.

Second, because the inhibitor primarily serves to inhibit the formation of clathrate hydrates, rather than to reverse such formation, it is important to treat the fluid prior to substantial formation of clathrate hydrates. As a wet petroleum fluid cools, it will eventually reach a temperature, known as the hydrate equilibrium dissociation temperature, or $T_{eq}$, below which hydrate formation is thermodynamically favored. A petroleum fluid's $T_{eq}$ will shift as the pressure applied to the fluid, and its composition, change. Various methods for determining a fluid's $T_{eq}$ at various fluid compositions and pressures are well known to those skilled in the art. Preferably, the fluid should be treated with the inhibitor when the fluid is at a temperature greater than its $T_{eq}$. It is possible, but not preferable, to introduce the inhibitor while the temperature is at or slightly below the fluid's $T_{eq}$, preferably before clathrate hydrates have begun to form.

The inhibitor's solubility over a wide range of temperatures is important for ensuring that the polymer can be effectively injected under typical field conditions. Most polymeric inhibitors exhibit lower critical solution temperature, or LCST behavior when dissolved in water or brine. As the temperature of such solutions is increased, the polymer reaches a temperature where it will precipitate out of solution. The temperature above which the polymer will precipitate out of its solution is known as the polymer's cloud point, or $T_{cp}$. Various methods for determining a polymer's $T_{cp}$ at various compositions and pressures are well known to those skilled in the art. When the inhibitor solution temperature exceeds the cloud point for a particular polymer, the polymer will precipitate out of solution.

It is important to convey the inhibitor solution to the petroleum fluid at a temperature lower than its cloud point. The cloud point for a given polymer solution is dependent upon several factors, including the polymer concentration, other components present in the solution (such as dissolved salts), and the ambient temperature and pressure of the solution. In many oil and gas production situations, the inhibitor is injected under conditions where the temperature of the petroleum fluid to which the inhibitor is added can range as high as 100° C.–150° C. (212° F.–302° F.) or more. Consequently, it is desirable to select a polymer that exhibits a cloud point greater than the anticipated temperature of the petroleum fluid. Alternatively, the inhibitor could be injected at some point in the production system where the temperature of the petroleum fluid is below the polymer solution's cloud point.

Sub-cooling is a measure of the effectiveness of a hydrate inhibitor. When a petroleum fluid contains hydrate-forming constituents, clathrate hydrates will begin to form rapidly at a given temperature. As the hydrate-forming constituents (typically gases) are consumed in forming clathrate hydrates, there is an abrupt and corresponding decrease in the volume of gas in the petroleum fluid as hydrates are formed. The temperature at which this abrupt decrease in the volume of gas is observed is known as the temperature of onset for hydrate formation, or $T_{os}$. Various methods known to those skilled in the art, such as the mini-loop procedure described below, may be used to determine a fluid's $T_{os}$. As noted above, the hydrate equilibrium dissociation temperature, or $T_{eq}$, is the temperature below which hydrate formation is thermodynamically favored in an aqueous/gas solution without an inhibitor present. A hydrate inhibitor's sub-cooling, or $T_{sub}$, is the difference between the $T_{eq}$ and the $T_{os}$. (Note the subcooling is not actually a temperature, but a difference, measured in degrees, between two temperatures.) Therefore, for a given pressure, the greater the sub-cooling temperature, the more effective the inhibitor. Typically, an aqueous sea salt/gas solution with no inhibitor present produces a $T_{sub}$ of about 3 to 4° C. (5 to 7° F.).

The surfactant polymers of the invention offer the unique advantage of effective hydrate inhibition, as measured by sub-cooling, combined with high cloud point temperatures.

The concentration of inhibitor present in the aqueous phase of a petroleum fluid will typically vary from about 0.01 percent by weight (wt %) to about 5 wt %, based upon the aqueous phase present in the fluid. Preferably, the inhibitor will be present at a concentration of from about 0.01 wt % to about 0.5 wt %. Most preferably, the inhibitor will be present in an aqueous phase at a concentration of from about 0.1 wt % to about 0.5 wt %. The effective amount of an inhibitor for a particular application can be determined by those skilled in the art, by considering the inhibitor's performance factors, the degree of inhibition required for the petroleum fluid, and the inhibitor's cost. A higher inhibitor concentration can be used to lower the temperature at which a hydrate blockage would occur.

Novel Inhibitors

The inhibitors of the invention may be represented by the following general formula:

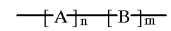

where the sum of n and m is an average number sufficient to produce a number average molecular weight between about 1,000 to about 6,000,000, and where A is the following surfactant mer-unit:

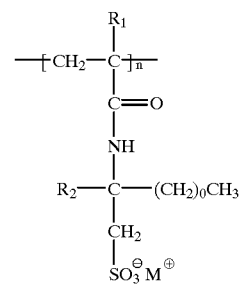

where $R_1$ and $R_2$ are independently hydrogen or a methyl group, and o is a number from 1 to 5. Preferably, o is a number from 1 to 3, and more preferably, o is a number from 1 to 2.

M is a metal cation selected from the group consisting of metals of Group IA of the Periodic Table, preferably sodium and potassium, and an ammonium cation. Sodium is most preferred. The corresponding anionic group is a sulfonate group, as shown above, but alternatively may be a sulfinate, sulfate, phosphonate, phosphinate, phosphate, or carboxylate group. Sulfonate and carboxylate groups are preferred, and sulfonate groups are most preferred. The two ionic groups are preferably associated as salts.

B may be a surfactant mer-unit that is the same as, or a variant of, A. If A and B are both surfactant mer-units, then one of A or B, for example, B, will have an o of from 1 to 3, while A may have an o of from 1 to 5. This will ensure that the resulting polysurfactant remains substantially water-soluble. The variation of the ratio of m to n will also impact polysurfactant solubility, and for the case described above, m:n would preferably range from 45:55 to 5:95, or from 45:55 to 25:75.

Alternatively, B is a monomer or mer-unit that is known, when polymerized with itself, to exhibit hydrate inhibition. For example, B may be an N-vinyl amide, an N-allyl amide, an acrylamide or methacrylamide, an N-vinyl lactam, a maleimide, or a vinyl oxazoline (a ring-closed cyclic imino ether).

The A and B mer-unit proportions, or mole ratio of m to n can vary. The mole ratio of m:n may vary from about 5:95 to about 95:5, or from about 25:75 to about 75:25, or from about 45:55 to about 55:45. Ratios which provide the most effective inhibitors for a given system are preferred.

In one alternative, the B mer-unit is an N-vinyl amide of the formula:

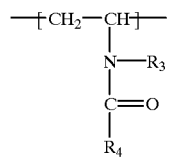

where $R_3$ is a hydrogen or a hydrocarbon group having one to six carbon atoms, and zero to two heteroatoms selected from the group consisting of oxygen, nitrogen, and combinations thereof, $R_4$ is a hydrocarbon group having one to six carbon atoms, and zero to two heteroatoms selected from the group consisting of oxygen and nitrogen and combinations thereof; and $R_3$ and $R_4$ have a sum total of carbon atoms greater than or equal to one, but less than eight. The $R_3$ and $R_4$ carbon atoms may be branched, normal, or cyclic; $R_3$ may be hydrogen or an alkyl, cycloalkyl, or aryl group; and $R_4$ is an alkyl, cycloalkyl, or aryl group.

Preferred N-vinyl amides include N-methyl N-vinyl acetamide, also known as N-vinyl N-methyl acetamide (VIMA).

Alternatively, the B mer-unit is an N-allyl amide of the formula:

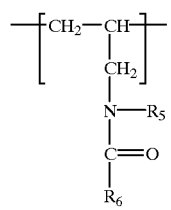

where $R_5$ is a hydrogen or hydrocarbon group having one to six carbon atoms, and zero to two heteroatoms selected from the group consisting of oxygen, nitrogen, and combinations thereof; $R_6$ is a hydrocarbon group having one to six carbon atoms, and zero to two heteroatoms selected from the group consisting of oxygen and nitrogen and combinations thereof;

$R_5$ and $R_6$ have a sum total of carbon atoms greater than or equal to one, but less than eight. The $R_5$ and $R_6$ carbon atoms may be branched, normal, or cyclic; $R_5$ is either hydrogen or an alkyl, cycloalkyl, or an aryl group; and $R_6$ is an alkyl, cycloalkyl, or an aryl group.

Alternatively, the B mer-unit is an acrylamide or methacrylamide of the formula:

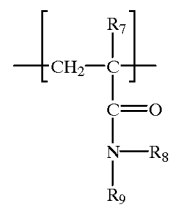

where $R_7$ is hydrogen or a methyl group; $R_8$ is a hydrocarbon group having one to ten carbon atoms, and zero to four heteroatoms selected from the group consisting of nitrogen, oxygen, sulfur, and combinations thereof; and $R_9$ is a hydrogen atom or a hydrocarbon group having one to ten carbon atoms, and zero to four heteroatoms selected from the group consisting of nitrogen, oxygen, sulfur, and combinations thereof; $R_8$ and $R_9$ have a sum total of carbon atoms greater than or equal to one, but less than eight. The $R_8$ and $R_9$ carbon atoms may be branched, normal, or cyclic; $R_8$ is an alkyl, cycloalkyl, or an aryl group; and $R_9$ is either hydrogen or an alkyl, cycloalkyl, or an aryl group.

Preferred acrylamides and methacrylamides are N-substituted acrylamides and N-substituted methacrylamides, such as isopropylacrylamide (IPA), methacryloylpyrrolidine (MAPYD) and N-isopropyl methacrylamide (IPMA).

Alternatively, the B mer-unit is an N-vinyl lactam of the formula:

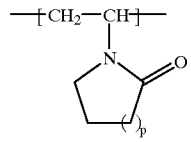

where p ranges from one to three, such as N-vinyl caprolactam (VCap), and N-vinyl pyrrolidone (VP), and N-vinyl piperidone (VPip). Preferred N-vinyl lactams include N-vinyl caprolactam (VCap), and N-vinyl pyrrolidone (VP), and VCap is particularly preferred.

The polymers and copolymers consistent with the description above form a class of materials designated "polysurfactants." By polysurfactants, we mean that there are pendant groups on the polymer backbone that resemble surfactant-like materials, i.e., there is a hydrophilic portion and a hydrophobic portion. The polysurfactants of the invention fall within the generic class of amphoteric polymers, those which contain hydrophilic and hydrophobic groups on the same mer-unit. An example is shown below for the case of the $C_6$ polysurfactant:

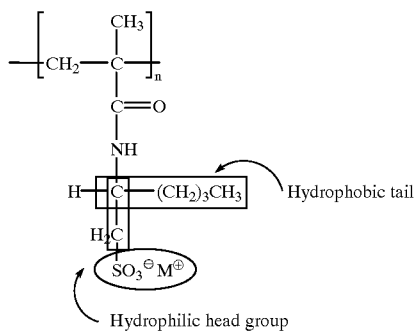

Hydrophobic tail

Hydrophilic head group

The designation of "$C_6$ polysurfactant" is based upon the number of carbon atoms below the nitrogen atom in the pendant group in the formula above, which results from the α-olefin used to produce the surfactant mer-unit.

To obtain an effective hydrate inhibitor, it is important to properly balance the hydrophobic and hydrophilic nature of the surfactant mer-unit. If the inhibitor is too hydrophobic, or has a hydrophobic chain that is too long, it will exhibit an undesirably low cloud point, and could become insoluble in water. If the inhibitor is too hydrophilic, due to a hydrophobic chain that is too short, the inhibitor will exhibit a subcooling that is too low for the material to be a good inhibitor, or may even promote hydrate formation.

Examples of polysurfactant copolymers of the type described above include materials such as:

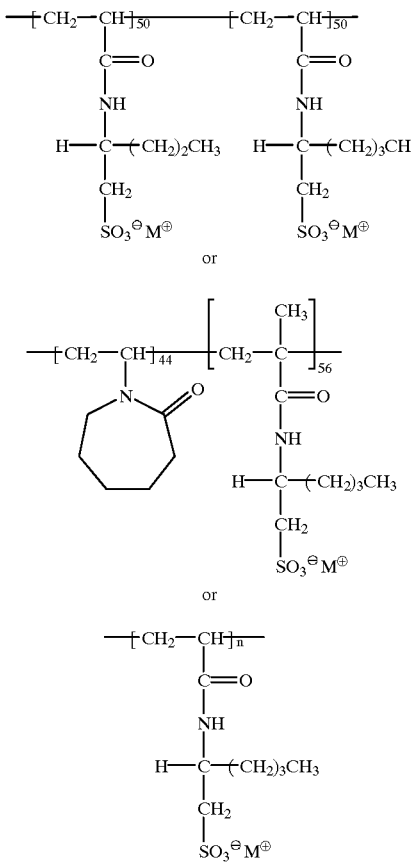

where M is sodium.

As mentioned above, B can comprise one or more mer-units known to inhibit hydrate formation. Thus, a further example of this invention is illustrated by the following terpolymer:

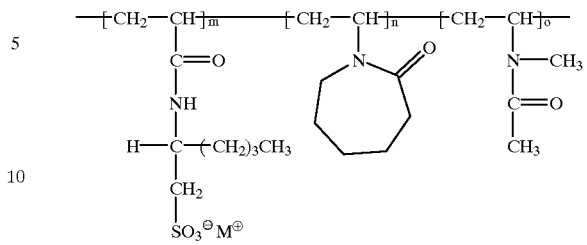

where M is sodium.

Due to the ionic nature of the polysurfactants of the invention, direct measurement of molecular weight by, for example, Gel Permeation Chromatography (GPC) is difficult. However, molecular weights of the polymers described above are expected to fall within the 1,000 to 6,000,000 number average molecular weight specified, based upon the structures identified and other polymerizations of this type.

The generic structures above as well as the examples given are intended to cover any substantially water soluble polymers including, but not limited to, copolymers, terpolymers, other complex polymers, and blends and mixtures thereof, having the structural units described, whether such structural units or their related monomers were used to synthesize the polymer or not. The monomers disclosed below for synthesizing the polymers containing the preferred mer-units are not intended to limit the scope of the claims. Other starting materials and synthesis techniques, which are currently known or may become known, will be apparent to those skilled in the art as alternatives to synthesizing the polymers of the claimed invention. Accordingly, all polymers having at least the structural unit identified in the claims below, even though such polymers may be produced from starting materials and/or by means not explicitly referenced herein, are intended to fall within the scope of the claimed invention. Other polymers not specifically identified in the examples below will become apparent to those skilled in the art in light of the detailed discussion below. Such polymers are intended to fall within the scope of the claimed invention.

The above-described polymers and copolymers can be used in a mixture with other polymers or additives useful for enhancing inhibitor performance, or operating parameters other than those specified here.

Experimental Results
Inhibitor Synthesis

Standard laboratory procedures familiar to those skilled in the art were used to synthesize the polymers and copolymers identified below. Benzene or low molecular weight alcohols were used as reaction solvents. Many common azo free radical initiators, such as 2,2'-azobis(2-methylpropionitrile), also known as AIBN, can be used for synthesizing copolymers. The polymers were isolated and characterized using techniques well-known to those skilled in the art, such as carbon-13 ($^{13}C$) and proton ($^1H$) nuclear magnetic resonance spectroscopy (NMR).

The surfactant monomers are prepared generally according to U.S. Pat. No. 5,036,136. The following is an illustrative procedure for the $C_6$ surfactant monomer:

A mixture of 21.0 g (31.2 mls) of 1-hexene and 55 g (68.2 mls) of acrylonitrile was cooled in an ice water bath. Subsequently, 28 g (14.4 ml) of fuming sulfuric acid (30 wt % sulfur trioxide dissolved in sulfuric acid) was added drop-wise under vigorous agitation. The procedure took approximately 25 minutes. The temperature of the mixture was allowed to warm to room temperature over a period of several hours. The agitated solution was stirred overnight. The product was filtered as a solid powder, and rinsed several times with acrylonitrile. The powder was dried in a vacuum oven at room temperature for 24 hours. NMR and elemental analysis were used to determine the molecular structure as well as the monomer purity. Using this same procedure, $C_4$–$C_8$ surfactant monomers were prepared. A methyl-substituted analogue, Me—$C_x$ surfactant monomer was also synthesized by treating methacrylonitrile with the appropriate α-olefin under acidic sulfonation conditions as described above.

EXAMPLE 1

Illustrative—$C_5$ Polysurfactant

The monomers prepared in Examples 1 and 2 were prepared by treating acrylonitrile with the appropriate α-olefin under acidic sulfonation conditions as described above. After the preparation of the monomers, homopolymerizations were run using the acidic form of the monomers (unless otherwise specified) in water as the reaction solvent and potassium persulfate as the free radical initiator. The reactions were run at 60° C. for a 16 hour period.

A 250 ml flask equipped with magnetic stir bar, thermometer, and a condenser with a nitrogen inlet/outlet was purged with nitrogen. 100 g of water, which had been degassed with nitrogen while cooled in an ice bath (1° C.), was loaded into the flask. Potassium persulfate (0.2 g; 7.4×10$^{-4}$ moles) was then added and stirred until dissolved while keeping the temperature at 1° C. Then $C_5$ surfactant (10 g, 0.045 moles) was added to the initiator solution and stirred for several minutes until dissolved. Once the monomer was dissolved, the reaction solution was polymerized by heating to 60° C. After 16 hours reaction time, the reaction was cooled and the polymer was neutralized with a slight excess of NaOH. The solution of the Na-salt of the polysurfactant was freeze-dried for 24 hours. The $^1$H NMR and $^{13}$C NMR of the polymer were consistent with the following structure:

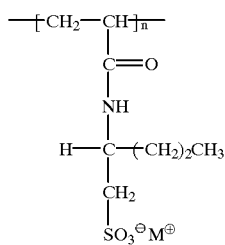

where M=Na, a poly(2-acrylamido-1-pentanesulfonic acid, sodium salt) polymer. When dissolved at 0.5 wt % in synthetic sea water, the polymer did not precipitate when heated to 100° C.; consequently, its $T_{cp}$ (at atmospheric pressure) was above 100° C.

EXAMPLE 2

Illustrative—$C_6$ Polysurfactant

The same procedure described in Example 1 above was used to make the $C_6$ polysurfactant, except that 10 g (0.042 mol) of the $C_6$ surfactant monomer was employed instead of the $C_5$ surfactant monomer. The $^1$H and $^{13}$C NMRs of the polymer product were consistent with the following structure:

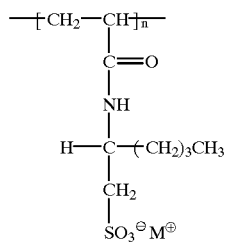

where M=Na, a poly(2-acrylamido-1-hexanesulfonic acid, sodium salt) polymer. This example was repeated using the same materials to make a second sample of the same polymer. When dissolved at 0.5 wt % in synthetic sea water, neither sample precipitated when heated to 100° C.; consequently, the $T_{cp}$ for these polymers (at atmospheric pressure) was above 100° C.

EXAMPLE 3

Illustrative—$C_7$ Polysurfactant

The same procedure described in Example 1 was used to make the $C_5$ polysurfactant, except that 10 g (0.040 mol) of the $C_7$ surfactant monomer was employed instead of the $C_5$ surfactant monomer. The $^1$H and $^{13}$C NMRs of the polymer product were consistent with the following structure:

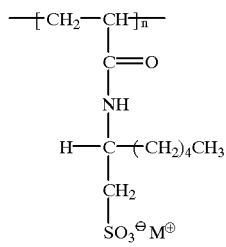

where M=Na, a poly(2-acrylamido-1-heptanesulfonic acid, sodium salt) polymer. The polymer had a cloud point (when dissolved in 0.5% synthetic sea water at atmospheric pressure) of 39° C.

EXAMPLE 4

Illustrative—Me—$C_6$ Polysurfactant Homopolymer

For this reaction, the Na salt of the monomer was used. The neutralization was carried out according to the following procedure: NaOH (4.01 g, 0.1003 moles) was dissolved in 583 g of deionized water and cooled to −3° C. by means of an icebath. Me—$C_6$ surfactant monomer (25 g, 0.1003 moles) was added slowly, making certain to maintain the temperature below 0° C. On completing the addition of the surfactant monomer, the pH of the solution was 2.5. The final pH was adjusted to 7.0 with a few drops of diluted NaOH, and the Na Me—$C_6$ surfactant monomer isolated by freeze drying.

To make the polymer, Na Me—$C_6$ surfactant monomer and 38 g water were charged to a 250 ml flask equipped with magnetic stir bar, thermometer, and a condenser with a nitrogen inlet/outlet. The solution was flushed for 1 hour with nitrogen. Then, the reaction was brought to 60° C. and ammonium persulfate (0.150 g, 6.6×10$^{-4}$ moles dissolved in 2 g water) was added. The reaction was heated at 60° C. and stirred under nitrogen overnight. The next day, the reaction solution was freeze dried for 24 hours. The resulting polymer was redissolved in MeOH and reprecipitated in diethyl ether. The $^1$H and $^{13}$C NMRs were consistent with the following polymer structure:

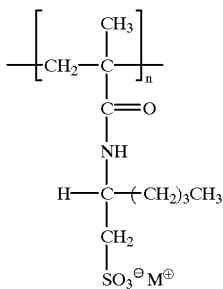

where M=Na, a poly(2-methacrylamido-1-hexanesulfonic acid, soldium salt) polymer. When dissolved at 0.5 wt % in synthetic sea water, the polymer did not precipitate when heated to 100° C.; consequently, its $T_{cp}$ (at atmospheric pressure) was above 100° C.

EXAMPLE 5

Illustrative—Copolymerization of $C_5$ Surfactant with $C_7$ Surfactant

Using the same general procedure described in Example 1 above, copolymers of the surfactant monomers can be made. Thus, a 250 ml flask equipped with magnetic stir bar, thermometer, and a condenser with a nitrogen inlet/outlet was purged with nitrogen. 100 g of water, which had been degassed with nitrogen while cooled in an ice bath (1° C.), was loaded into the flask. Potassium persulfate (0.2 g 7.4×10$^{-4}$ moles) was then added and stirred until dissolved while keeping the temperature at 1° C. Then 4.7 g (0.021 moles) $C_7$ surfactant and 5.3 g (0.021 moles) $C_7$ surfactant were added to the initiator solution and stirred for several minutes until dissolved. Once the monomers were dissolved, the reaction solution was polymerized by heating to 60° C. After 16 hours reaction time, the reaction was cooled and the copolymer was neutralized with a slight excess of NaOH. The solution of the Na-salt of the polysurfactant was freeze-dried for 24 hours. The $^1$H and $^{13}$C NMRs of the copolymer were consistent with the following structure:

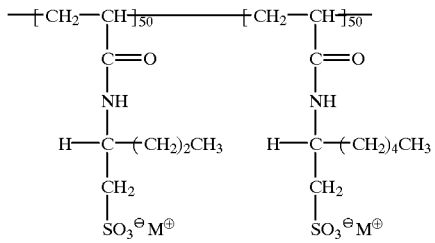

where M=Na, a poly(2 acrylamido-1-pentanesulfonic acid-co-2-acrylamido-1-heptanesulfonic acid), sodium salt copolymer. When dissolved at 0.5 wt % in synthetic sea water, the polymer did not precipitate when heated to 100° C.; consequently, its $T_{cp}$ (at atmospheric pressure) was above 100° C.

EXAMPLE 6

Illustrative—Copolymerization of $C_5$ Surfactant and $C_7$ Surfactant

The procedure outlined in Example 5 above was used to prepare a 50/50 copolymer of the monomers of Examples 1 and 2, a poly(2-acrylamido-1-pentanesulfonic acid-co-2-acrylamido-1-octanesulfonic acid), sodium salt copolymer. When dissolved at 0.5 wt % in synthetic sea water, the polymer did not precipitate when heated to 100° C.; consequently, its $T_{cp}$ (at atmospheric pressure) was above 100° C.

EXAMPLE 7

Illustrative—Copolymerization of $C_6$ Surfactant with IPMA

N-isopropylmethacrylamide (IPMA) was purchased from Aldrich Chemical Company and recrystallized twice from hexane. Anhydrous methanol was purchased from Aldrich Chemical Company. Deionized water was degassed by sparging with nitrogen. The initiator, 2,2'-Azobis (2-amidinopropane) hydrochloride (V50) was obtained from WAKO Pure Chemical Industries and used as received. The $C_6$ surfactant, prepared as described in Example 2, was neutralized with NaOH as described above in Example 4.

Na—$C_6$ surfactant (13.37 g, 0.052 moles) and IPMA (6.62 g, 0.052 moles) were charged to a 3-necked flask equipped with a condenser, stirrer, nitrogen inlet/outlet and thermometer. The powders were purged with nitrogen for about 1 hour. Then, 90 g MeOH and 90 g water, which had been purged separately, were added together to the reaction flask. The reaction mixture was brought to 60° C., then initiated with 0.6 g (2.2×10$^{-3}$ moles) V50, which was dissolved in a H$_2$O/MeOH mixture. The reaction was maintained at a constant temperature of 60° C. while it was stirred overnight. The next day, MeOH was removed from the reaction mixture on a rotary evaporator. The remaining water/polymer mixture was freeze-dried for 24 hours. This remaining product had $^1$H and $^{13}$C NMRs consistent with the following structure:

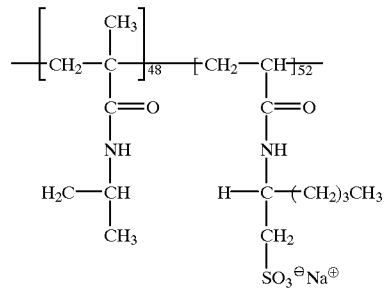

a poly(2-acrylamido-1-hexanesulfonic acid, sodium salt-co-N-isopropyl-methacrylamide) copolymer. When dissolved at 0.5 wt % in synthetic sea water, the polymer did not precipitate when heated to 100° C.; consequently, its $T_{cp}$ (at atmospheric pressure) was above 100° C.

EXAMPLE 8

Illustrative—Copolymerizations of Me—$C_6$ Surfactant with IPMA

Using a procedure similar to that outlined in the Example 7, the sodium salt of the Me—$C_6$ surfactant monomer was copolymerized with IPMA, using MeOH/water mixtures as the solvent. The initiator, 2,2'-azobis methyl butyronitrile (V67) was obtained from DuPont Chemicals, and used as received. A table summarizing the recipes used follows:

| Example | IPMA | NaMeC$_6$ | V67 | H$_2$O/MeOH | Reaction Temp | Copolymer Composition (IPMA/NaMeC$_6$) |
|---|---|---|---|---|---|---|
| 8A/8B | 3.38 g (0.027 mol) | 6.62 g (0.027 mol) | 0.3 g (0.0016 mol) | 10 g/20 g | 64° C. | 48.4/51.6 |
| 8C/8D | 5.43 g (0.043 mol) | 4.57 g (0.018 mol) | 0.3 g (0.0016 mol) | 10 g/20 g | 64° C. | 72.3/27.7 |

The copolymers were isolated by precipitating the reaction mixture into diethylether, followed by filtration. The products were then redissolved in MeOH and reprecipitated in diethylether. The $^1$H and $^{13}$C NMRs were consistent with the formation of poly(2-methacrylamido-1-hexanesulfonic acid, sodium salt-co-N-isopropyl-methacrylamide) copolymers. When dissolved at 0.5 wt % in synthetic sea water, the Example 8A polymer did not precipitate when heated to 100° C., consequently its T$_{cp}$ (at atmospheric pressure) was above 100° C. The Example 8C copolymer had a cloud point (when dissolved in 0.5 wt % synthetic sea water at atmospheric pressure) of 80–82° C.

EXAMPLE 9

Illustrative—Copolymerizations of Me—C$_6$ Surfactant with VCap

A 100 ml 4-necked round bottom flask loaded with a mechanical stirrer, condenser, thermometer, and N$_2$ inlet/outlet, was charged with N-vinylcaprolactam (VCap) (1.79 g, 0.0129 moles), which was used as received from Scientific Polymer Products. The flask was flushed with N$_2$ for over 1 hour, then 6 ml of anhydrous MeOH was added. The solution was heated to 64° C. Azobisisobutyronitrile (AIBN) (0.0150 g in 4 ml MeOH) was then added to the VCap solution. NaMeC$_6$ surfactant (3.21 g, 0.0129 mole) was dissolved in 9.6 g of deionized H$_2$O, flushed with N$_2$, and loaded in a 25 cc syringe. This solution was then pumped into the VCap solution at a rate of 0.064 g NaMeC$_6$ per minute for about 50 minutes. A pumping procedure was used to achieve a random copolymer, due to the unequal reactivities of the two monomers employed here. The reaction was stirred and heated overnight. The following day, the reaction mixture was precipitated into acetone and filtered. The polymer was further purified by redissolving in acetone and reprecipitating into diethyl ether. The $^1$H and $^{13}$C NMRs were consistent with the following structure:

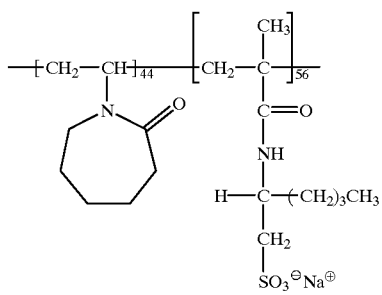

a poly(N-vinyl caprolactam-co-1-methacrylamido-1-hexanesulfonic acid, sodium salt) copolymer. The copolymer had a cloud point (when dissolved in 0.5% synthetic sea water at atmospheric pressure) of 35° C.

EXAMPLE 10

Comparative—Poly (Na-AMPS), Poly (IPMA), and Poly (VCap)

A sample of poly (2-arylamido-2-methyl-1-propanesulfonic acid sodium salt) or Poly (AMPS) was obtained from Polysciences Inc. (Warrington, Pa.). This polymer may be represented by the following structure:

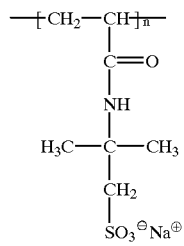

a poly(2-acrylamido-2-methyl-1-propanesulfonic acid, sodium salt) polymer. This material was evaluated as a comparative example, and was not expected to be an effective inhibitor. Although it falls within the class of amphoteric polymers, it is not considered a polysurfactant, since it has no hydrophobic tail, and consequently it is too hydrophilic.

Samples of poly(N-isopropyl methacrylamide) or poly (IPMA), poly(N-vinyl caprolactam) or poly(VCap), and a copolymer of N-vinyl pyrroliddone (VP) and VCap, or poly VP/VCap, were obtained from previous work and used for comparison with the inhibitors of the invention. In addition, copolymers of AMPS with VCap, VP, and a combination of VP and VCap, were also prepared and used for comparison with the inhibitors of the invention. These polymers and copolymers may be synthesized by procedures known to those skilled in the art.

Mini-loop Testing Procedure

One method for evaluating an inhibitor's effectiveness uses a bench-scale high pressure apparatus referred to as a mini-loop apparatus. A mini-loop apparatus consists of a loop of stainless steel tubing with about a one-half inch inside diameter and about ten feet in length. The loop also has a transparent section for observing the fluid flow in the loop and the onset of hydrate formation in the loop. Fluid comprising about 40% by volume (vol %) synthetic sea water solution having about 3.5% total ionized salts, 40 vol % hydrocarbon condensate (i.e., C$_6$+), and 20 vol % hydrocarbon gas mixture is circulated around the loop at constant pressure. The hydrocarbon gas mixture is comprised of approximately 85 mole % methane, 5 mole % ethane, 5 mole % propane, and 5 mole % of C$_4$+. The inhibitor is typically injected into the loop as an aqueous solution to produce the desired weight percent (wt %) concentration of inhibitor in the aqueous sea salt/gas solution. Generally, hydrate inhibitors are evaluated at about 0.5 wt % of the aqueous sea salt/gas solution.

The fluid is circulated at a constant velocity of about 0.76 m/second (2.5 feet/second). The loop and its pump are operated in a controlled temperature water bath to control the temperature of the fluid circulating in the loop. The bath water is circulated to ensure uniform temperature throughout the bath and rapid heat transfer between the bath water and the loop. As the loop temperature changes or as hydrates form, the gas volume in the loop will change accordingly. Therefore, to maintain constant pressure in the loop, a pressure-compensating device is required. Such a device can be comprised of a gas cell and a hydraulic oil cell separated by a floating piston. As the gas volume in the loop changes, oil may be added or removed from the oil cell to produce a commensurate addition or removal of gas to the loop. Mini-loop tests are typically run at a pressure of about 6996 KPa absolute (1,000 pounds per square inch gauge (p.s.i.g.)). However, any pressure between 101 to 20,786 KPa absolute (0 to 3,000 p.s.i.g.) could be selected for evaluating an inhibitor's performance.

The temperature of the water bath is reduced at a constant rate, preferably about 6° F. (3.3° C.) per hour, from an initial temperature of about 70° F. (21° C.). At some temperature, clathrate hydrates begin to rapidly form. As gas is consumed in forming clathrate hydrates, there is an abrupt and corresponding decrease in the volume of gas in the fluid as hydrates are formed. The temperature at which the abrupt decrease in the volume of gas is observed is measured as the temperature of onset for hydrate formation, or $T_{os}$, and compared to the hydrate equilibrium dissociation temperature, or $T_{eq}$, to determine the inhibitor's subcooling. A hydrate inhibitor's subcooling, or $T_{sub}$, is the difference between the $T_{eq}$ and the $T_{os}$. (Note the subcooling is not actually a temperature, but a difference, measured in degrees, between two temperatures.) For a given pressure, the greater the subcooling, the more effective the inhibitor.

Mini-loop Test Results

For the purpose of illustrating the invention, the various polymeric inhibitors described above were evaluated using the mini-loop testing procedure described above. The results of these evaluations are provided in the Table below.

The data show that the polysurfactant homopolymers and copolymers of the invention are effective inhibitors with a good balance of properties. The polysurfactant inhibitors of the invention are generally more effective (as measured by subcooling) than other known amphoteric polymers, such as poly(AMPS). Furthermore, copolymers of surfactant monomers copolymerized with monomers of effective hydrate inhibitors, such as poly(VCap) and poly(IPMA), are better inhibitors than the corresponding VCap and IPMA homopolymers. This is an unexpected result. Typically, properties and performance of copolymers are the additive of the two homopolymers. These systems exhibit an unexpected synergy.

The polysurfactant homopolymers and copolymers of the invention are also advantageous because they generally have higher cloud points than other known inhibitors. Polymeric inhibitors other than poly (AMPS) typically exhibit cloud point temperatures (under atmospheric conditions) of less than 100° C., and typically in the range of about 20° C. to about 40° C., for previously-known polymeric inhibitors which exhibit good subcooling properties. The surfactant monomers of the invention, when polymerized with monomers whose homopolymers have low cloud points, such as poly(VCap) and poly(IPMA), serve to raise the cloud point of the resulting inhibitors. Most of the polysurfactant copolymers of the invention have cloud points above 100° C., while exhibiting subcoolings that indicate they are effective hydrate inhibitors. Thus, most of these inhibitors can be applied near the wellhead, where the hottest temperatures would be experienced, without precipitation.

The means and method for practicing the invention and the best mode contemplated for practicing the invention have been described. It is to be understood that the foregoing is illustrative only and that other means and techniques can be employed without departing from the true scope of the invention as claimed herein.

We claim:

1. A method for inhibiting the formation of clathrate hydrates in a fluid having hydrate-forming constituents, the

TABLE 1

| Example | Inhibitor | Polymer Mole Ratio | Conc. (wt %) | Subcooling (° F.) | Subcooling (° C.) | Cloud Point (° C.) |
|---|---|---|---|---|---|---|
| ILLUSTRATIVE | | | | | | |
| Example 1 | $C_5$ polysurfactant | NA | 0.5 | 17 | 9.4 | >100° |
| Example 2A | $C_6$ polysurfactant | NA | 0.6 | 19.5 | 10.8 | >100° |
| Example 2B | $C_6$ polysurfactant | NA | 0.5 | 20.5 | 11.4 | >100° |
| Example 3 | $C_7$ polysurfactant | NA | 0.5 | 14 | 7.8 | 39° |
| Example 4 | $MeC_6$ polysurfactant | NA | 0.5 | 19 | 10.6 | >100° |
| Example 5 | $C_5/C_7$ copolysurfactant | 50:50 | 0.5 | 20 | 11.1 | >100° |
| Example 6 | $C_5/C_8$ copolysurfactant | 50:50 | 0.5 | 19 | 10.6 | >100° |
| Example 7 | $C_6$ surfactant/IPMA Copolymer | 52:48 | 0.5 | 24.5 | 13.6 | >100° |
| Example 8A | $MeC_6$ surfactant/IPMA Copolymer | 48:52 | 0.5 | 25 | 13.9 | >100° |
| Example 8B | $MeC_6$ surfactant/IPMA Copolymer | 48:52 | 0.5 | 26 | 14.4 | — |
| Example 8C | $MeC_6$ surfactant/IPMA Copolymer | 28:72 | 0.5 | 27 | 15.0 | 80–82° |
| Example 8D | $MeC_6$ surfactant/IPMA Copolymer | 28:72 | 0.5 | 27 | 15.0 | — |
| Example 9 | $C_6$ surfactant/VCap Copolymer | 56:44 | 0.5 | 31 | 17.2 | 35° |
| COMPARATIVE | | | | | | |
| Example 10A | Poly (AMPS) | NA | 0.5 | 14.4 | 8.0 | >100° |
| Example 10B | Poly (IPMA) | NA | 0.5 | 24.0 | 13.3 | 38° |
| Example 10C | Poly (VCap) | NA | 0.5 | 22.5 | 12.5 | 27° |
| Example 10D | Poly (AMPSNCap) | 50:50 | 0.5 | 17 | 9.4 | >100° |
| Example 10E | Poly (AMPSNP) | 50:50 | 0.5 | 12 | 6.7 | >100° |
| Example 10F | Poly (VP/VCap/AMPS) | 29:22:49 | 0.5 | 22 | 12.2 | 67° |
| Example 10G | Poly (VP/VCap) | 50:50 | 0.5 | 21 | 11.7 | 55° | method comprising contacting the fluid with an inhibitor wherein the inhibitor comprises a substantially water-soluble polymer having a plurality of the following surfactant unit:

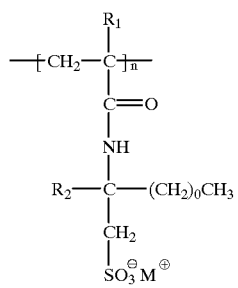

where,
R$_1$ is hydrogen or a methyl group,
R$_2$ is hydrogen or a methyl group,
o is an integer from 1 to 5,
M is a cation selected from the group consisting of sodium, potassium, and ammonium ions, and
n is an average number of units for producing a number average molecular weight for the polymer between about 1,000 and about 6,000,000.

2. The method of claim 1, wherein o is from 1 to 3.
3. The method of claim 1, wherein the polymer is a homopolymer.
4. The method of claim 1, wherein o is from 1 to 2.
5. The method of claim 3, wherein the surfactant unit is represented by the formula:

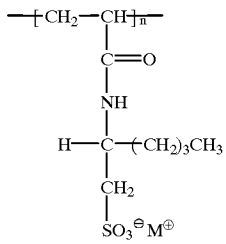

wherein M is sodium.
6. The method of claim 1, wherein the polymer is a copolymer having a plurality of two different surfactant units.
7. The method of claim 6, wherein the copolymer is represented by the formula:

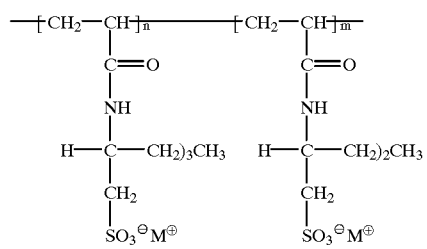

wherein the ratio m:n ranges from 45:55 to 5:95, and M is sodium.
8. The method of claim 1, wherein the polymer is a copolymer having a plurality of the surfactant unit and a plurality of a comonomer unit selected from the group consisting of acrylamides, methacrylamides, N-allyl amides, N-vinyl amides, and N-vinyl lactams.

9. The method of claim 8 wherein the inhibitor is a copolymer having a mole ratio of surfactant units to comonomer units of from about 25:75 to about 75:25.

10. The method of claim 8 wherein the inhibitor is a copolymer having a mole ratio of surfactant units to comonomer units of from about 45:55 to about 55:45.

11. The method of claim 8, wherein the comonomer unit is an acrylamide or methacrylamide represented by the formula:

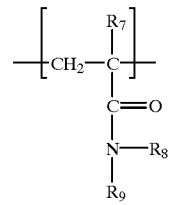

where,
R$_7$ is hydrogen or a methyl group;
R$_8$ is a hydrocarbon group having one to ten carbon atoms, and zero to four heteroatoms selected from the group consisting of nitrogen, oxygen, sulfur, and combinations thereof; and
R$_9$ is a hydrogen atom or a hydrocarbon group having one to ten carbon atoms, and zero to four heteroatoms selected from the group consisting of nitrogen, oxygen, sulfur, and combinations thereof.

12. The method of claim 11 wherein the comonomer unit is an N-substituted methacrylamide selected from the group consisting of methacryloylpyrrolidine and N-isopropyl methacrylamide.

13. The method of claim 8, wherein the comonomer unit is an N-vinyl amide represented by the formula:

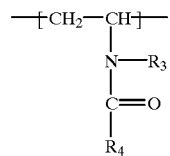

where,
R$_3$ is a hydrogen atom or a hydrocarbon group having one to six carbon atoms, and zero to two heteroatoms selected from the group consisting of oxygen, nitrogen, and combinations thereof,
R$_4$ is a hydrocarbon group having one to six carbon atoms, and zero to two heteroatoms selected from the group consisting of oxygen, nitrogen, and combinations thereof, and
R$_3$ and R$_4$ have a sum total of carbon atoms greater than or equal to one, but less than eight.

14. The method of claim 13 wherein the N-vinyl amide is N-methyl N-vinyl acetamide.

15. The method of claim 8, wherein the comonomer unit is an N-vinyl lactam represented by the formula:

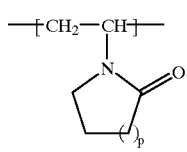

where p is 1 to 3.

16. The method of claim 15, wherein the N-vinyl lactam is N-vinyl caprolactam.

17. The method of claim 8 wherein the comonomer unit is an N-allyl amide of the formula:

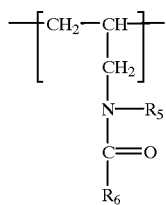

where
- $R_5$ is a hydrogen atom or a hydrocarbon group having one to six carbon atoms, and zero to two heteroatoms selected from the group consisting of oxygen, nitrogen, and combinations thereof,
- $R_6$ is a hydrocarbon group having one to six carbon atoms, and zero to two heteroatoms selected from the group consisting of oxygen, nitrogen, and combinations thereof, and
- $R_5$ and $R_6$ have a sum total of carbon atoms greater than or equal to one, but less than eight.

18. The method of claim 1 wherein the water-soluble polymer is a copolymer, the copolymer is mixed with a carrier solvent prior to treating the fluid, and wherein the carrier solvent is selected from the group consisting of water, brine, sea water, produced water, methanol, ethanol, propanol, isopropanol, glycol, and mixtures thereof.

19. The method of claim 18 wherein the inhibitor is provided in an aqueous solution, and the fluid is a petroleum fluid.

20. The method of claim 19 wherein the inhibitor is present in the fluid at a concentration of from 0.01 wt % to about 0.5 wt % of the water present in the fluid.

* * * * *